United States Patent
Schmitt et al.

(12) 
(10) Patent No.: US 6,499,159 B1
(45) Date of Patent: Dec. 31, 2002

(54) APPARATUS FOR COUPLING A DRIVE TO AN ADJUSTABLE PATIENT POSITIONING PLATE IN A MEDICAL SYSTEM

(76) Inventors: Guenter Schmitt, Forststr. 16, 91056 Erlangen (DE); Rolf Reimann, Raiffeisenstr. 24, 91301 Forchheim (DE); Karlheinz Barde, Haidenaab 35, 95469 Speichersdorf (DE)

( * ) Notice: Subject to any disclaimer, the term of this patent is extended or adjusted under 35 U.S.C. 154(b) by 0 days.

(21) Appl. No.: 09/576,762

(22) Filed: May 24, 2000

(30) Foreign Application Priority Data

Jun. 28, 1999 (DE) .......................................... 199 29 654

(51) Int. Cl.[7] .............................................. A61G 13/02
(52) U.S. Cl. .............................. 5/601; 5/943; 74/89.38; 192/84.9; 378/209
(58) Field of Search ........................... 5/601, 943, 600; 374/209; 192/84.9; 74/89.38

(56) References Cited

U.S. PATENT DOCUMENTS

| | | | | |
|---|---|---|---|---|
| 3,588,500 A | * | 6/1971 | Koerner ........................ | 5/601 |
| 4,426,715 A | | 1/1984 | Baer et al. .................... | 378/4 |
| 4,761,000 A | * | 8/1988 | Fischer et al. ................ | 5/601 |
| 5,329,657 A | * | 7/1994 | Bartley et al. ............. | 74/89.38 |

* cited by examiner

*Primary Examiner*—Alexander Grosz

(57) ABSTRACT

In a coupling arrangement for a drive arrangement and an adjustable positioning plate of a medical system, the positioning plate is adjustable at least in the direction of its longitudinal axis via the drive arrangement as well as by hand. A friction connection between the drive arrangement and the positioning plate can be produced and cancelled via the coupling arrangement such that the positioning plate can be adjusted at least in the direction of its longitudinal axis via the drive arrangement given a friction connection, and by hand given a neutralized friction connection. The coupling arrangement acts directly between the drive arrangement and the positioning plate.

9 Claims, 6 Drawing Sheets

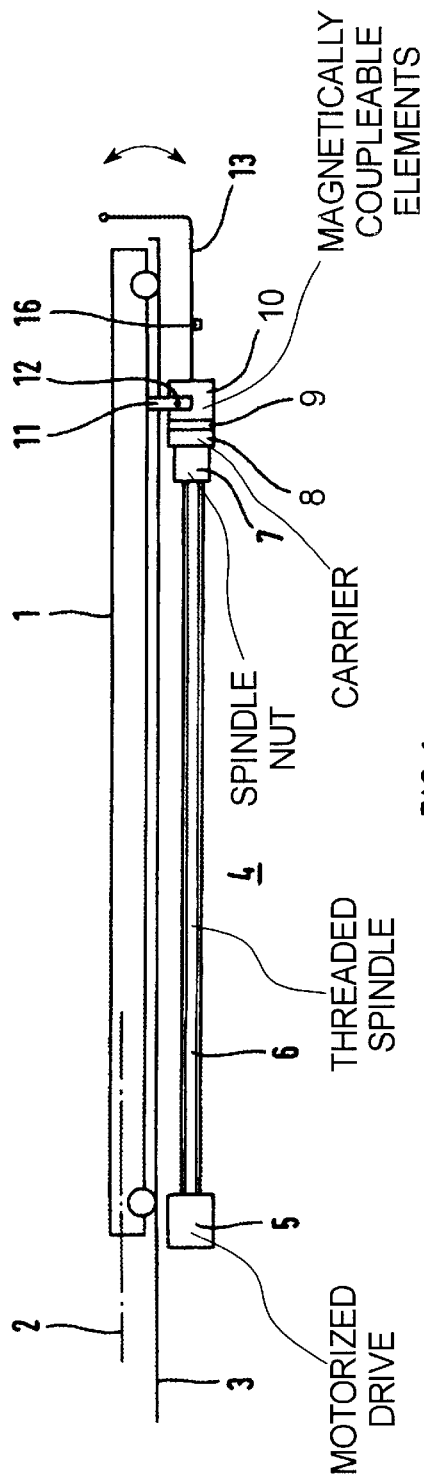
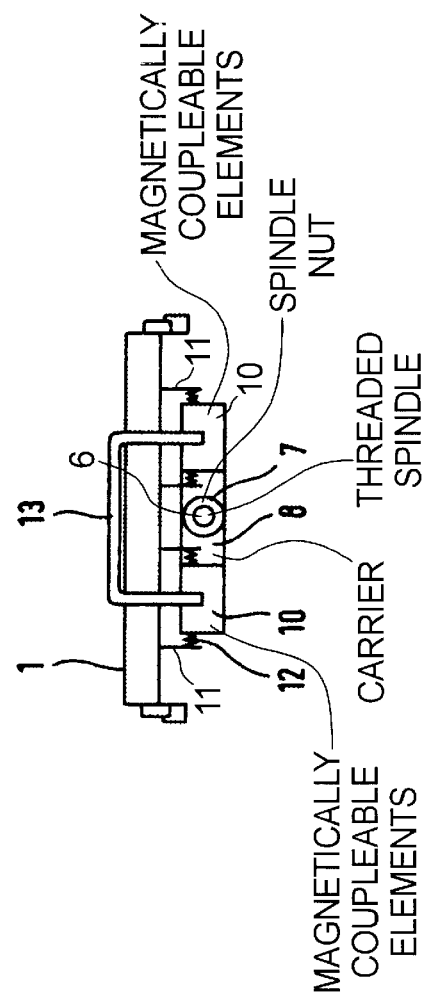

APPARATUS FOR COUPLING A DRIVE TO AN ADJUSTABLE PATIENT POSITIONING PLATE IN A MEDICAL SYSTEM

BACKGROUND OF THE INVENTION

1. Field of the Invention

The present invention is directed to an arrangement for coupling and decoupling a drive mechanism from an adjustable patient positioning plate, of the type used in a medical diagnostic or treatment system.

2. Description of the Prior Art

Patient positioning tables are employed in medical systems in order to position examination subjects, particularly patients, for specific medical examinations and/or treatments. An exact adjustment and positioning of the positioning plate of such a patient positioning table must be assured in radiological examinations, particularly computed tomography examinations, magnetic resonance examinations as well as radiation treatment, but also for other treatments, whereby a subject must be positioned exactly, particularly reproducibly, with resect to a treatment instrument or device. For adjustment of the positioning plate, it is known to provide a drive that has a toothed belt guided on wheels at which engages the positioning plate for adjustment. A drive motor is connected to at least one of these wheels via a controllable coupling means. In the coupled state, it is cosequently possible to adjust the positioning plate via the drive at least along its longitudinal axis. A precise positioning of the patient for the diagnostic or therapy system is consequently possible. In addition, it makes the work of the medical personnel easier since no exertion is required. In order to make it possible to quickly adjust the positioning plate given a power outage or for medical treatment of the patient, the drive can be decoupled from the wheel, so that the positioning plate is adjustable at least along its longitudinal axis. This is then particularly advantageous when the patient is introduced into a tube or a tunnel for the treatment, as is required for computed tomography or magnetic resonance examinations. When the patient is to be examined or treated further, e.g. after the medical treatment, then the patient must be positioned with the positioning plate optimally exactly at the original examination treatment location. The use of encoders and reference switches at the drive in connection with the drive means and/or the positioning plate is known.

The adjustment of the positioning plate into the examination position ensues on the basis of the signals of the encoders via the drive motor and is controlled by software.

German OS 3126 643 discloses a radiation diagnosis device having a means for adjusting a positioning device for an examination subject using a stepping motor in conjunction with a spindle.

SUMMARY OF THE INVENTION

An object of the present invention is to implement a coupling arrangement of the type initially described wherein the positioning plate can be decoupled from the drive arrangement in a simple fashion, and wherein a precise re-coupling to the drive arrangement as well as an exact re-positioning of the positioning plate are possible after decoupling and adjusting the positioning plate.

The above object is achieved in accordance with the principles of the present invention in a patient positioning apparatus having a motorized drive and an adjustable positioning plate, and a coupling arrangement directly connected between said drive and said positionable plate which is selectively operable to couple said drive to said plate, allowing adjustment of the plate along its longitudinal axis by the drive, and to decouple the drive from the plate, thereby allowing manual adjustment of the positioning plate. Coupling and decoupling takes place by making and breaking a coupling retention. The retention can be produced magnetically or mechanically.

An advantage of the invention is that the positioning plate is adjustable at least in the direction of its longitudinal axis via the drive arrangement as well as by hand. Using a coupling arrangement to cancel a retention connection between the drive arrangement and the positioning plate, the positioning plate is adjustable at least along its longitudinal axis via the drive arrangement given a retention connection, and by hand given a canceled retention connection. The coupling arrangement inventively acts directly between the drive arrangement and the positioning plate, so that slackness or imprecision do not arise, as are caused in convention devices by the elasticity of the toothed belt or due to the graduation of the encoder.

It is advantageous to implement the coupling arrangement as a magnetic arrangement, particularly having at least one permanent magnet. Such permanent magnets are inexpensive, in that they do not require energy in order to produce or cancel the magnetic fields.

The coupling arrangement can have at least one magnetic plate and a permanent magnet, with the plate and the permanent magnet being rotatable relative to one another around an axis, the rotation ensuing via a lever. Coupling is thereby achieved in a simple fashion between the plate and the permanent magnet, and thus between the positioning plate and the drive arrangement in a simple and precise way.

As an alternative to magnetic coupling, a mechanical coupling with limited linkage play can also be used.

It is particularly advantageous, when the drive arrangement has a drive mechanism that engages and rotates a threaded spindle for longitudinal displacement of the positioning plate. The spindle is in communication with the positioning plate via a spindle nut and the coupling arrangement. A very precise positioning of the positioning plate is possible via the spindle in conjunction with the spindle nut.

In a first version of an exemplary embodiment of the invention, a carrier engages the spindle nut, and extends at least approximately vertically to the longitudinal axis of the spindle, and has at least one area with magnetic material. At least one magnetic element allocated to the area is arranged at the positioning plate, the magnetic element being in communication with a lever, with which it can swivel around the swivel axis, and the magnetic connection can be neutralized by swiveling the lever. According to an alternative version of the invention, at least one carrier extends from the spindle nut at least approximately vertically to the longitudinal axis of the spindle for at least one magnetic element, and at the positioning plate, at least one magnetic area allocated to the magnetic element is provided. The magnetic area is in communication with a lever, with which it can be swivelled around the swivel axis, and the magnetic connection can be canceled by swivelling the lever. Thus, a precise coupling and decoupling between the drive arrangement and the positioning plate is assured in a simple fashion.

In order to assure symmetrical forces and consequently to avoid a tilting of the positioning plate, the spindle and the spindle nut, it is advantageous when the coupling arrangement has two sub-arrangements on both sides of the center axis of the positioning plate that are linked to one another via the lever.

To compensate tolerances, it is advantageous when the magnetic devices, or the magnetic areas, are seated so as to be adjustable in a direction along the swivel axis.

DESCRIPTION OF THE DRAWINGS

FIG. 1 is a schematically side view of a first exemplary embodiment of the coupling arrangement according to the invention, shown schematically.

FIG. 2 is an end view of the coupling arrangement according to FIG. 1.

DESCRIPTION OF THE PREFERRED EMBODIMENTS

Figure 3:
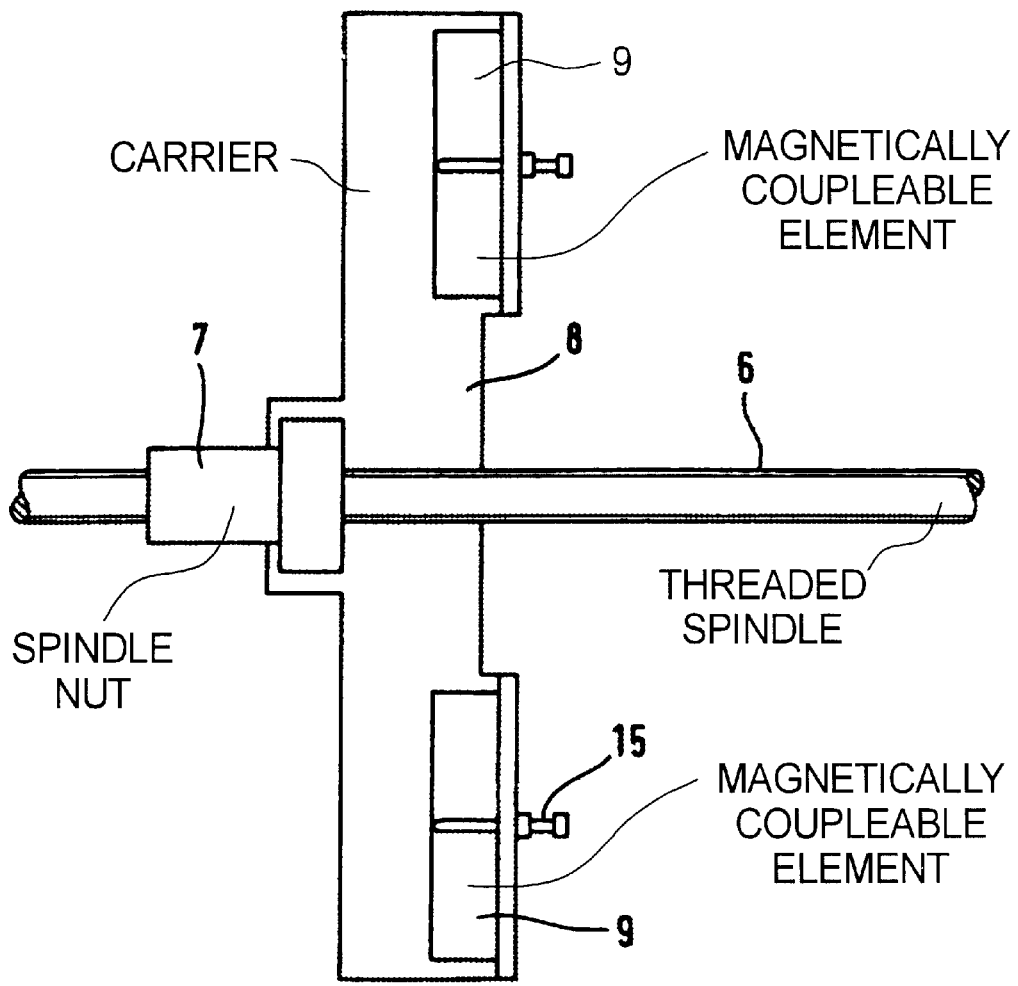
FIG. 3 shows a carrier of a first part of the coupling arrangement according to FIGS. 1 and 2, the carrier being in communication with a spindle nut.

Identical elements are identified by identical reference characters in the Figures. FIG. 1 schematically shows a positioning plate 1 of a medical system, e.g. of a diagnostic and/or therapy device and/or treatment device, the positioning plate being adjustable at least along its longitudinal axis 2 at least one guide rail or track 3. A drive arrangement is generally identified by the reference character 4 and, in the exemplary embodiment, includes a motorized drive 5 that is in communication with a threaded spindle 6. It is, however, also possible to implement the drive arrangement 4 such that it has a motorized drive that engages at a belt extending along the length of the adjustment path of the positioning plate 1 for adjustment purposes. In the preferred development, a spindle nut 7 is provided that is adjustable along the spindle 6 via the motorized drive 5. A coupling exists between the motorized drive 5 and the spindle 6, which is seated to rotate around its longitudinal axis. A carrier 8 oriented at least approximately vertically to the longitudinal axis of the spindle 6 is in communication with the spindle nut 7, and has at least one first magnetically coupleable element 9. This carrier 8 is a first part of the inventive coupling arrangement. A second part (FIG. 4) of the inventive coupling arrangement has a second magnetically coupleable element 10 that is connected to the positioning plate 1 via a bracket 11. The first magnetically coupleable element 9 can be an area or plate of magnetic material, and the second magnetically coupleable element 10 can be a magnet, or vice versa. The second coupleable element 10 can rotate in the bracket 11 around an axis 12, preferentially by a lever 13. Via the bracket 11 and its attachment mechanisms at the positioning plate 1, it is possible to finely adjust the position of the second magnetically coupleable element 10 with respect to the first magnetically coupleable element 9 by means of, e.g. oblong holes provided at the bracket 11.

It can be seen from FIG. 1 that the drive arrangement 4 is in communication with the positioning plate 1 via the inventive coupling arrangement. By operating the motorized drive 5 to rotate the spindle 6 around its longitudinal axis, the spindle nut 7 and thereby the positioning plate 1 (via the coupling arrangement) are adjusted along the longitudinal axis. A decoupling ensues by rotating the element 10 around the axis 12 with the lever 13. Upon rotation, the magnetic force between the element 10 and the element 9 is reduced due to the increasing air gap which arises as the substantially flat-mating surfaces of the element 9 and 10 separate and thus the coupling can be cancelled. Given a decoupling, the positioning plate 1 can be adjusted by hand along its longitudinal axis 2 and away from the spindle nut 7. In order to reduce any remaining retention force between the element 10 and the element 9, an adjustable element, e.g. a screw 15 (FIG. 3) can be provided, at which the element 10 rests upon rotation around the axis 12. A screw 15 is suited since an adjustment can thereby ensue in a simple fashion.

Figure 4:
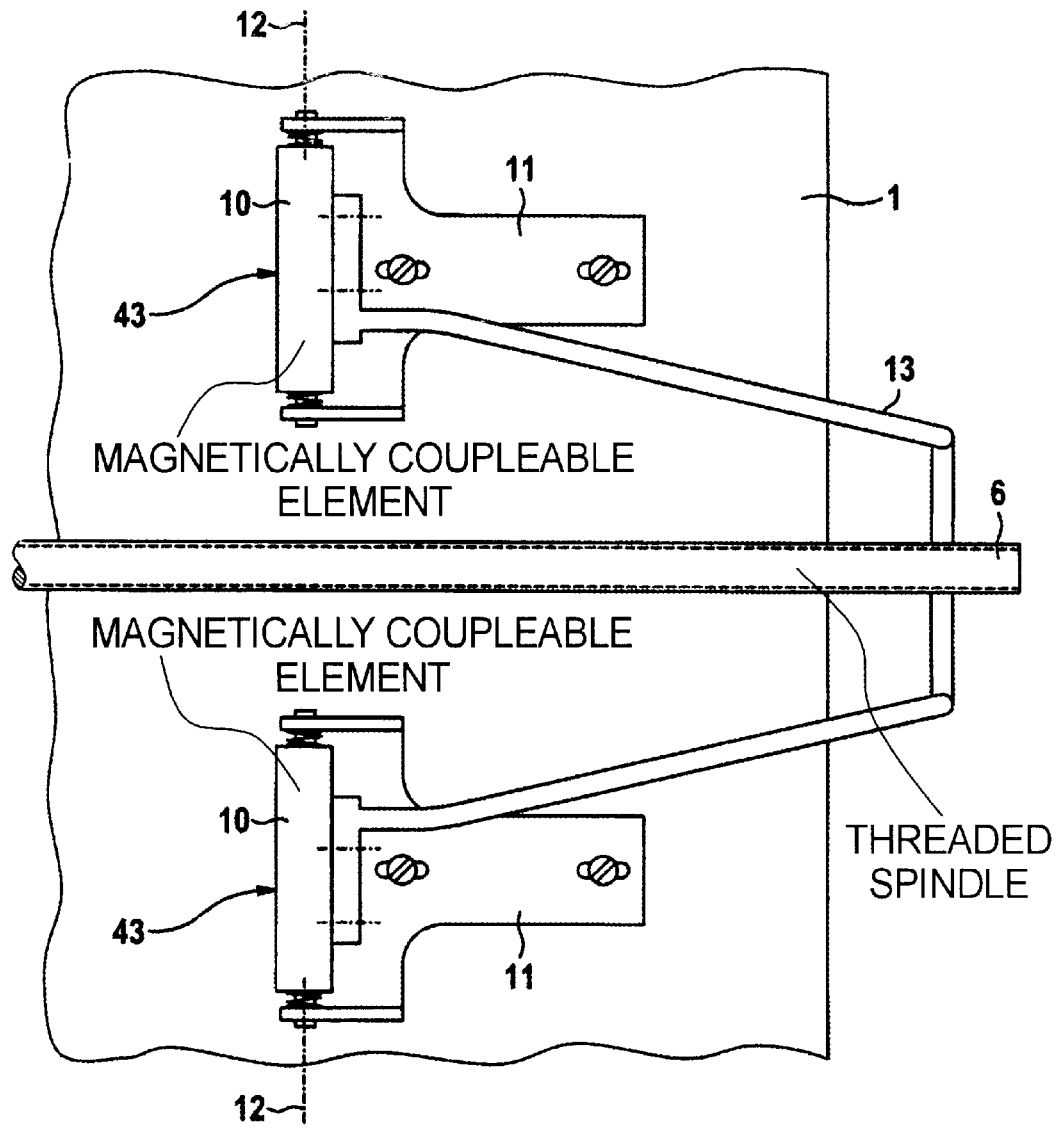
FIG. 4 shows a second part of the coupling arrangement according to FIG. 1, as seen from below the poisoning plate.

As can be seen in FIG. 4 the element 10 is seated to be resiliently adjustable along the axis 12, for which, e.g. spring elements can be provided on both sides of the element 10. Any positioning inaccuracy thus can be compensated between the element 10 and the element 9.

It further proceeds from FIGS. 3 and 4 that inventive coupling arrangements can be respectively provided on both sides of the spindle 6, that is preferably arranged along the center of the positioning plate 1, in order to thus avoid tilting during adjustment of the positioning plate 1. During coupling and decoupling as well, this dual arrangement avoids tilting and asymmetrical forces at the spindle nut 7 and thereby at the spindle 6. According to FIG. 1, the L-shaped lever 13 is lifted upward for decoupling in the exemplary embodiment. For coupling, the lever 13 is brought into the position shown in FIG. 1 where it lies, e.g. on a bearing 16. In this state, the positioning plate I is adjusted in the direction of the spindle nut 7 until a magnetic coupling ensues. In this manner, very high positioning accuracy and reproducibility of the position of the positioning plate 1 become possible.

Figure 6:
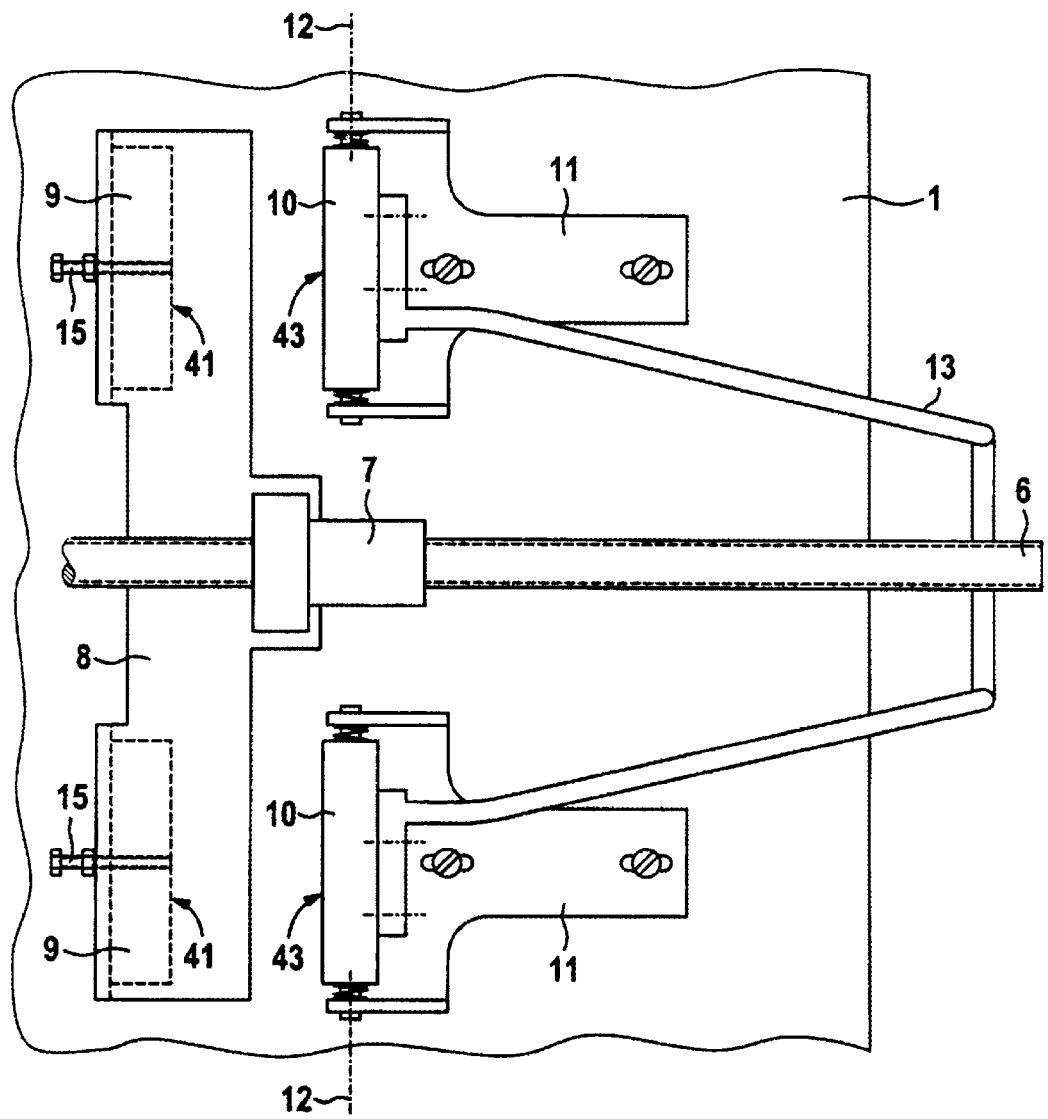
FIGS. 6 and 7 show all components of the coupling arrangement of FIG. 1, as seen from below the positioning plate, in a decoupled position and a coupled position, respectively.
Figure 7:
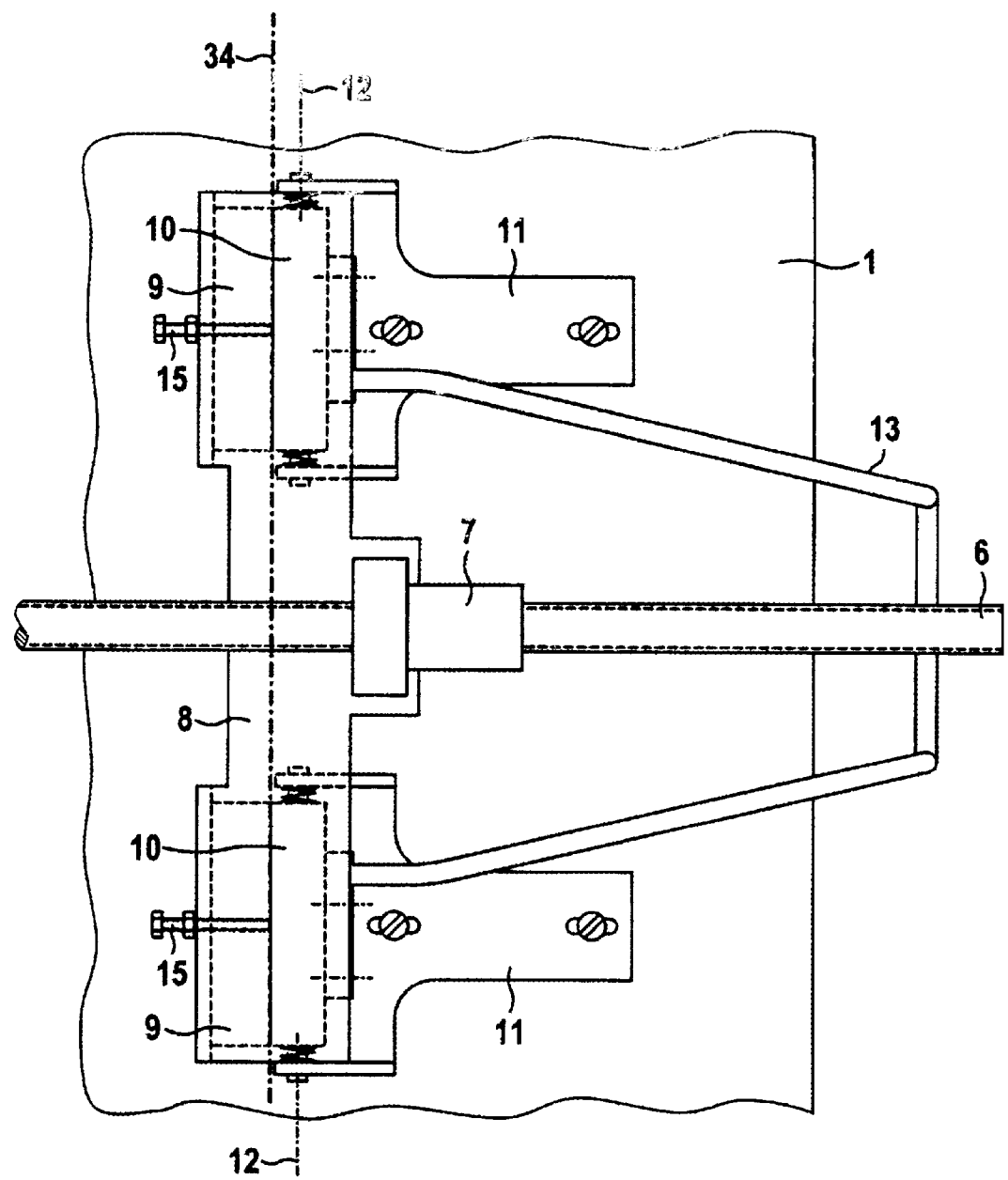

FIG. 6 shows the coupling arrangement as seen from below in FIG. 1 in a decoupled state, wherein the components shown separately in FIGS. 3 and 4 are shown in their combined orientation. As can be seen in FIG. 6, the elements 9 on the carrier 8 respectively have surfaces 41 which face toward surfaces 43 of respective elements 10. In the coupled state shown in FIG. 7, these surfaces are adjacent to each other and define a contact plane 34 at which non-positive magnetic coupling occurs. After such coupling, further rotation of the spindle 6 causes adjustment of the position of the table 1. When the handle 13 is moved upwardly or downwardly as indicated by the arrows in FIG. 1, the coupling along the contact plane 34 is broken and further rotation of the spindle 6 then causes the components to again separate, to the state shown in FIG. 6.

Figure 5:
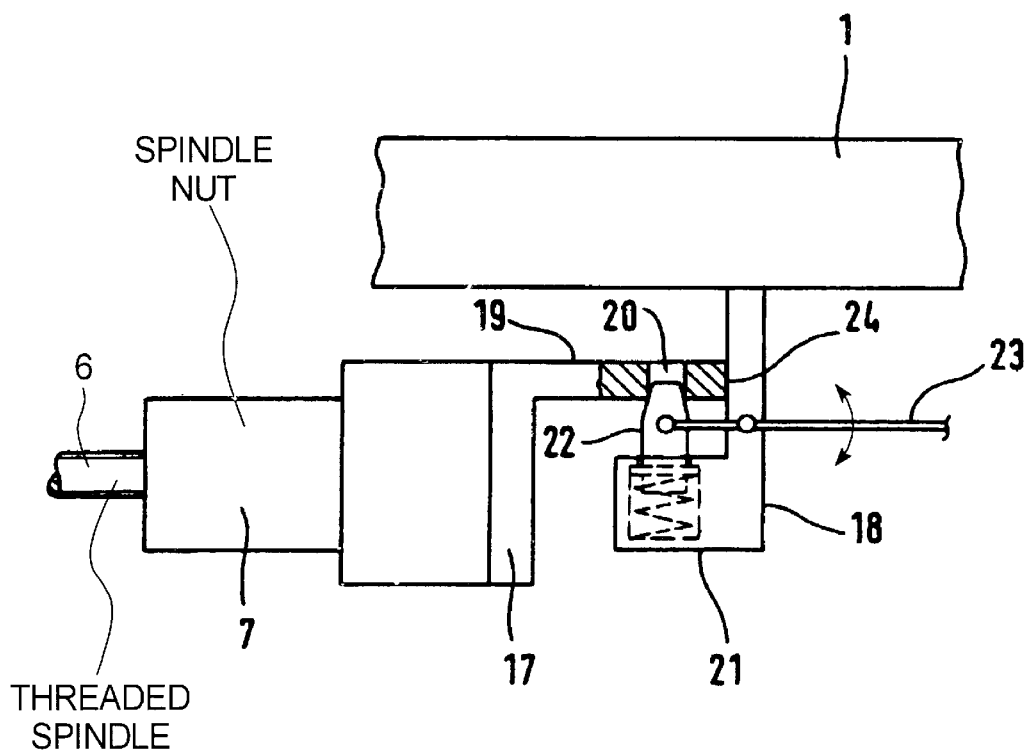
FIG. 5 shows a second exemplary embodiment of a mechanical coupling arrangement according to the invention.

A further exemplary embodiment is shown in FIG. 5 that is implemented as a mechanical coupling with limited linkage play. Therein, a first L-shaped coupling element 17 is arranged at the spindle nut 7. A second, e.g. L-shaped coupling element 18 is in communication with the positioning plate 1. For this exemplary embodiment, a recess 20 is provided at a first leg 19 of the first L-shaped coupling element 17, into which a peg 22 arranged at the first leg 21 of the second L-shaped coupling element 18 can engage. For this purpose, the peg 22 is seated to be elastically adjustable in the direction of the recess 22 and adjustable out of the recess 20 by a lever 23. To enable an easy engagement of the peg 22 into the recess 20, its area near the recess 20 is provided with beveled surfaces. In the coupled state, for example, the end-face side 24 of the first leg 19 of the first L-shaped coupling element 17 meets at the second leg of the second L-shaped coupling element 18 in order to thus define a position of the positioning plate 1 relative to the spindle nut 7. In order to fix this position with limited mechanical play, the peg 22 engages into the recess 20 as shown. The positioning plate 1 is thus linked to the drive arrangement via the spindle nut 7 and is thereby adjustable. For release of this coupling, the peg 22 can be moved out of the recess 20 with the lever 23, whereby a decoupling ensues and the positioning plate I can be adjusted by hand along its longitudinal axis 2 away from the spindle nut 7. In this exemplary embodiment it is also possible to provide a corresponding, mechanical coupling arrangement on both sides of the spindle nut 7, i.e. symmetrical to the centerline of the positioning plate 2, in order to avoid said tilting.

If only one coupling arrangement is provided, this is then ably disposed in the area of the spindle axis 6 in order to avoid tilting upon coupling and decoupling. Consequently, a somewhat more economical design results.

Although modifications and changes may be suggested by those skilled in the art, it is the intention of the inventors to embody within the patent warranted hereon all changes and modifications as reasonably and properly come within the scope of their contribution to the art.

We claim as our invention:

1. A patient positioning apparatus for use in a medical system, comprising:

a motorized drive;

an adjustable positioning plate having a longitudinal axis and being movable along said longitudinal axis; and a magnetic coupling arrangement disposed directly between said drive and said plate and being operable to selectively make and break a non-positive magnetic coupling to selectively couple said drive to said plate for adjusting said plate along said longitudinal axis by said drive, and to selectively decouple said plate from said drive to allow manual adjustment of said plate along said longitudinal axis.

2. An apparatus as claimed in claim 1 wherein said magnetic coupling arrangement comprises a first magnetically coupleable element and a second magnetically coupleable element which produce said non-positive magnetic coupling.

3. An apparatus as claimed in claim 2 wherein said first magnetically coupleable element is connected to said drive, and wherein said second magnetically coupleable element is connected to said plate, and wherein said magnetic coupling arrangement further comprises a lever connected to said second magnetically coupleable element operable to move said second magnetically coupleable element into and out of magnetic retention with said first magnetically coupleable element.

4. An apparatus as claimed in claim 3 wherein said first magnetically coupleable element comprises an element of magnetic material and wherein said second magnetically coupleable element comprises a magnet.

5. An apparatus as claimed in claim 3 wherein said first magnetically coupleable element comprises a magnet and said second magnetically coupleable element comprises an element of magnetic material.

6. An apparatus as claimed in claim 2 wherein said drive comprises a drive mechanism, a threaded spindle having a longitudinal axis and a spindle nut engaging said threaded spindle and connected to said magnetic coupling arrangement, said threaded spindle being rotatable around said longitudinal axis by said drive mechanism to move said plate when said coupling arrangement couples said drive via said threaded nut to said plate.

7. An apparatus as claimed in claim 6 wherein said magnetic coupling arrangement comprises a carrier connected to said spindle nut, said first magnetically coupleable element being carried by said carrier and having a first surface, and wherein said second magnetically coupleable element has a second surface, said first and second surfaces mating with each other to magnetically couple said drive to said plate, and said first and second surfaces being separated from each other upon rotation of said second magnetically coupleable element to break said magnetic coupling to decouple said drive from said plate.

8. An apparatus as claimed in claim 7 wherein said magnetic coupling arrangement comprises a bracket connected to said plate, said second magnetically coupleable element being pivotably mounted in said bracket for rotation around an axis, and said second magnetically coupleable element being laterally adjustable along said axis to position said second surface relative to said first surface.

9. An apparatus as claimed in claim 1 wherein said plate has a longitudinal center axis, and wherein said magnetic coupling arrangement is a first magnetic coupling arrangement, and said apparatus further comprising a second magnetic coupling arrangement, identical to and simultaneously operable with said first magnetic coupling arrangement, said first and second magnetic coupling arrangements being disposed symmetrically on opposite sides of said center axis of said plate.

* * * * *